United States Patent
Hattori et al.

(10) Patent No.: US 7,182,962 B2
(45) Date of Patent: Feb. 27, 2007

(54) IMMUNOSTIMULATOR FOR ANIMALS AND HUMANS, AND METHOD OF PREVENTING ANIMAL AND HUMAN INFECTIOUS DISEASES AND CANCER

(75) Inventors: Tsuneo Hattori, Ames, IA (US); Yukinori Takahashi, Yamaguchi Prefecture (JP); Yoshihiro Tachikawa, Kanagawa Prefecture (JP)

(73) Assignee: APC Company, Inc., Ames, IA (US)

( * ) Notice: Subject to any disclaimer, the term of this patent is extended or adjusted under 35 U.S.C. 154(b) by 258 days.

(21) Appl. No.: 10/699,810

(22) Filed: Nov. 3, 2003

(65) Prior Publication Data

US 2004/0197342 A1   Oct. 7, 2004

Related U.S. Application Data

(63) Continuation of application No. 09/808,840, filed on Mar. 15, 2001, now abandoned.

(60) Provisional application No. 60/191,211, filed on Mar. 22, 2000.

(51) Int. Cl.
*A61K 35/16* (2006.01)
*A61K 45/00* (2006.01)
*A61K 38/00* (2006.01)
*A23K 1/17* (2006.01)
*C07K 1/00* (2006.01)

(52) U.S. Cl. .................. 424/530; 424/278.1; 424/442; 514/2; 530/830; 530/362; 530/363

(58) Field of Classification Search ............ 424/278.1, 424/530, 9.2, 442; 530/362, 363, 300, 830; 514/2
See application file for complete search history.

(56) References Cited

U.S. PATENT DOCUMENTS

| | | | |
|---|---|---|---|
| 4,262,022 A | 4/1981 | Hald-Christensen et al. | 426/32 |
| 4,396,634 A | 8/1983 | Shenouda et al. | 426/104 |
| 5,556,643 A | 9/1996 | Bohanon et al. | 424/602 |
| 5,562,919 A | 10/1996 | Doty et al. | 424/464 |
| 5,575,999 A | 11/1996 | Yoder | 424/94.6 |
| 6,004,576 A | 12/1999 | Weaver et al. | 424/442 |
| 6,156,333 A | 12/2000 | Langrehr | 424/442 |
| 6,168,803 B1 | 1/2001 | Harris et al. | |

FOREIGN PATENT DOCUMENTS

| | | |
|---|---|---|
| EP | 0 503 959 | 6/1985 |
| JP | 58098061 A | 6/1983 |
| JP | 361132143 A | 6/1986 |
| JP | 62040251 A | 2/1987 |
| JP | 06086627 A | 3/1994 |
| WO | WO-99/07236 | 2/1999 |

OTHER PUBLICATIONS

Stahly et al. ISU Swine Research Report, pp. 3-5, 1994.*
Markowska-Daniel et al. Polish J. Vet. Sci. 6: 275-277, 2003.*
Suetsuna, K. , et al., "Effect of Porcine Plasma Protein and Peptide on Cellular Immunologic Response", *Shokuniku ni kansuru Josei Kenkyu Chosa Seika Hokokusho*, vol. 10, with USPTO translation,(1991),328-334.
"Illustrated Stedman's Medical Dictionary, 24th Edition, 1982, p. 707".
"Ref. No. XP-002142456".
"Takefman et al. J. Virol. 75: 4551-4557, 2001, abstract".
"The Webster's II New Riverside University Dictionary, 1984, p. 933".
Itami, Toshiaki , et al., "Enhancement of disease resistance of kuruma shrimp, Penaeus japonicus, after oral administration of peptidoglycan derived from Bifidobacterium thermophilum", *Aquaculture 164*, 277-288.
Maeda, Minoru , et al., "Effect of Various Treatments on White Spot Syndrome Virus (WSSV) from Penaeus japonicus (Japan) and P. monodon (Thailand)", *Fish Pathology*, 33(4), 381-387.

* cited by examiner

*Primary Examiner*—S. Devi
(74) *Attorney, Agent, or Firm*—Schwegman, Lundberg, Woessner & Kluth, P.A.

(57) ABSTRACT

The goal of the present invention is to provide substances to prevent diseases by activating inherently possessed functions, for cultured fishes and shellfishes and livestock with tendency of decreased immune function due to densely populated breeding environment, and for humans with tendency of easily lowered immune functions due to complicated social structures and aging. The present invention expresses marked effect in preventing infection and cancer by administrating appropriate dose of swine plasma, swine plasma albumin, peptides isolated from swine plasma and swine plasma albumin, and swine plasma mixture, among others including fine powder of Crustacea (including crust of Crustacea), to activate immune function of Crustacea, Pisces, Aves, Mammals, and humans.

4 Claims, No Drawings

IMMUNOSTIMULATOR FOR ANIMALS AND HUMANS, AND METHOD OF PREVENTING ANIMAL AND HUMAN INFECTIOUS DISEASES AND CANCER

CROSS-REFERENCE TO RELATED APPLICATIONS

This application is a continuation of U.S. application Ser. No. 09/808,840, filed Mar. 15, 2001, now abandoned, which claims priority to U.S. Provisional Application Ser. No. 60/191,211 filed on Mar. 22, 2000, the disclosures of which applications are incorporated by reference herein.

FIELD OF THE INVENTION

The invention relates generally to an immunostimulator of all animals and humans, feed, veterinary pharmaceuticals, beverages, food, health food, and pharmaceuticals containing said immunostimulator, infectious diseases that are subject for administration of said immunostimulator, and prevention method of cancer; more particularly, the invention relates to immunostimulation, immunostimulator that shows marked effectiveness in infectious disease and cancer prevention, administration to animals and humans of feed, veterinary pharmaceuticals, beverages, food, health food, and pharmaceuticals containing said immunostimulator in appropriate ratio for preventing infectious disease and cancer of animals and humans.

BACKGROUND OF THE INVENTION

With the development in cultured fishery of Pisces and Crustacea, frequent incidences of viral and bacterial infection became prevalent, causing significant damage. Piscine disease such as tuberculoid and streptococcus infection of yellowtail, *Favobacterium psychrophilim* infection of sweetfish, iridovirus infection of red sea bream and yellowtail, and Crustacean disease such as acute viremia or vibrionic disease of kuruma prawn, cause severe damage. Incidence rates are high in diseases of livestock, including cattle, swine, and fowl, such as diarrhea of calf, atrophic rhinitis and pleuropneumonia of swine, infectious bronchitis and *E. coli* infection of fowl. For these bacterial diseases, antibiotics and synthetic antibacterial agents are being used; however, resistant strains have emerged, and satisfactory therapeutic effect has not been achieved. Also, residual drug remained after use in the body of fish and livestock have caused public health problem; therefore, preventive measure that do not depend on the use of chemical treatment is necessary.

Effective therapeutic treatment for viruses has not yet been discovered for viral diseases of Pisces and Crustacea, and the progress is slow in the development of vaccines. Vaccines are used in some viral diseases of livestock, but as in cases of avian infectious bronchitis, the effectiveness is not sufficient; thus, there are still frequent incidences.

On the other hand, human infectious disease such as MRSA infection, VRE infection, enterohemorrhagic *E. coli* infection, tuberculosis, influenza, and diseases such as cancer are frequent. Many of the frequently occurring diseases of today are caused by bacteria, which have gained resistance to drugs previously effective in treating diseases caused by these bacteria; therefore, novel compound with antibacterial activity to these resistant strains are expected. Moreover, as the background of above mentioned disease occurring frequently, decreased human immune function due to stress and other factors are accounted for. Unless these underlying problems are solved, antibiotics and conventional anticancer agent cannot be the effective countermeasures in current state.

For the purpose of stimulating immune functions and preventing infectious diseases in fishes and shellfishes and animals, using substances such as component of bacterial cell wall from bacillus (Japanese Patent Publication No. 03-173826, and Japanese Patent Publication No. 04-193823), *Bifidobacterium thermophilum* derived peptidoglycan (Japanese Patent Publication No. 06-25067), and −1, 3-glucan derived from *Schizophyllum commune* (Japanese Patent Publication No. 06-65649) are already known. Furthermore, swine derived purified plasma (Japanese Patent Publication No. 59-88042) with antibacterial activity and containing antibody to enteropathogenic *E. coli*, is being used for the purpose of preventing *E. coli* infection of neonatal animals, and for the purpose of increasing palatability of feed to piglets, proteins (Japanese Patent Publication No. 07-16366) with albumin and globulin isolated from swine or bovine blood as major ingredient have been in use.

The substance of the present invention, does not show antibacterial activity to enteropathogenic *E. coli*, or other bacteria, or does not prevent *E. coli* infection or other bacterial disease of neonatal animals by agglutinating *E. coli* or other bacteria by specific antigen, but peptide contained in swine plasma prevent infectious diseases of animals and humans by fortifying non-specific and specific bio-defense mechanisms such as phagocytotic activity, complement activity, lysozyme activity, cytokine production ability, and antibody production ability by acting on granulocyte of Crustacea, leukocyte of Pisces, and T lymphocyte, B lymphocyte, and macrophage of vertebrate including humans. Therefore, said substance of present invention differs in mechanism of action as well as object of usage from swine derived purified plasma (Japanese Patent Publication No. 59-88042), previously mentioned. Thus, said substance of present invention that stimulate immune function is not a substance present in swine or bovine globulin (antibody, or antibacterial substance), but peptide in albumin, as clearly disclosed in embodiments. Moreover, since the major constituent of present invention stimulate immune function of animals and humans, present invention differs in terms of effective constituent and object of usage from the substance of [Japanese Patent Publication No. 07-16366], previously mentioned. Therefore, said substance of present invention is an immunostimulator that actively stimulate immune function of animals and humans, and unrelated to immunoglobulin (antibodies) or palatability enhancing substance.

Recently, as substances to strengthen human immune function, *Agaricus blazei*, -carotene, chitin, and chitosan among others are used; however, these immunostimulator differs from antibiotics or antibody in such way that they do not show increasing effect depending on increased dose of intake, and the effect is not displayed unless appropriate dose is taken [Chihara G. The mechanism of bio-defense. ed.: Mizuno—et al., (in Japanese) Tokyo, University of Tokyo Press; 1983: 302–318, and Takahashi Y et al. Gekkan Kaiyo (Marine Monthly, in Japanese). 1998; 14(suppl): 154–158]. Therefore, the current state, which sales are conducted without any research on upper limit and lower limit of effective dose, is quite problematic.

As described above, numerous cases of infection occurred among Pisces, Crustacea, and other animal, cause significant damage. As the background of these incidence, the decrease of immune function due to breeding in small area and in crowded condition is considered. It is thus the object of the present invention to provide substance for Pisces, Crustacea, and other animal to be bred safe and free from public health problem such as residual drug, while preventing infection by markedly increasing immune function that is inherent to fishes and shellfishes and animals.

With respect to the human conditions, various types of stress are exerted upon humans due to economic depression and complication of social structure, and decrease of immune function occur with aging; consequently, incidence of infections that were previously not problematic, or of cancer are frequent. In order to prevent these diseases, many substances that stimulate immune function have been on market as food or pharmaceuticals, but these are sold without the sure knowledge of appropriate dose. As already described, immunostimulator has upper limit and lower limit in its effective dose, and unless administered within this appropriate dose range, immune function is not stimulated. Additionally, it is an object of the present invention to provide substance and method to maintain health by properly activating human immune function that tends to decrease due to stress and aging, with the appropriate intake of said substance of present invention.

Further, it is an object of the present invention to prevent infectious disease and cancer of humans and all animals such as Crustacean, Pisces, Aves, and mammals, by fortifying non-specific and specific bio-defense mechanisms such as phagocytotic activity, complement activity, lysozyme activity, phenol oxidase activity, cytokine production ability, and antibody production ability, using the action of peptide contained in swine plasma on granulocyte of Crustacea, leukocyte of Pisces, and T lymphocyte, B lymphocyte, NK cells and macrophage of mammals and humans.

SUMMARY OF THE INVENTION

The present inventors have discovered, in the course of pursuing present invention, that each administration of peptide purified from swine plasma (albumin), plasma albumin containing the peptide as active ingredient, or plasma to animals such as Pisces and Crustacea, the immune function inherent to these animals was activated and consequently prevents infections by bacteria and virus. Also, in order to investigate the optimum dose of the said substance of present invention, we administered the said substance in various doses to animals; as a result, we discovered that the optimum daily dose per kg of animal's body weight were: 1–300 mg swine plasma albumin-derived peptide, especially 5–100 mg was the optimum dose; 30–1000 mg in case of swine plasma albumin, especially 70–500 mg was the optimum dose; 100–3000 mg in case of swine plasma or swine plasma mixed with fine-powdered Crustacea or crust of Crustacea, especially 200–1200 mg was the optimum dose. Moreover, the rats given the said substance displayed the enhanced anti-tumor activity and suppression of tumor cell proliferation, and we identified those humans who were administrated the said substance of present invention had significantly lowered rate of cold and influenza incidence.

The present invention provides immunostimulator for animals and humans, containing swine plasma as active ingredient, and is characterized by expressing immunostimulative activity, infection preventing effect, and anti-tumor effect on Crustacea, Pisces, other vertebrates, and humans. The present invention further provides immunostimulator for animals and humans containing swine plasma albumin as active ingredient, and is characterized by expressing immunostimulative activity, infection preventing effect, and anti-tumor effect on Crustacea, Pisces, other vertebrates, and humans. In addition, the present invention provides immunostimulator for animals and humans containing swine plasma as active ingredient, and is characterized by expressing immunostimulative activity, infection preventing effect, and anti-tumor effect on Crustacea, Pisces, other vertebrates, and humans. Moreover, the present invention provides immunostimulator for animals and humans containing swine plasma, swine plasma albumin, or peptides mixed with fine-powdered Crustacea, fine-powdered crust of Crustacea, or purified materials from Crustacea or crust of Crustacea.

Additionally, the present invention provides feed, veterinary pharmaceuticals, beverages, food, health food, and pharmaceuticals containing said immunostimulator as in one of claims 1–4. Further, the present invention provides a method of preventing infectious disease and cancer of animals and humans characterized by administration or use of feed, veterinary pharmaceuticals, beverages, food, health food, and pharmaceuticals. Moreover, the present invention provides a method of preventing infectious disease and cancer of animals and humans characterized by administration or using of 1–300 mg swine plasma (albumin)-derived peptide, more preferably, 5–100 mg; 30–1000 mg in case of swine plasma albumin, more preferably, 70–500 mg; 100–3000 mg in case of swine plasma or swine plasma mixed with fine-powdered Crustacea or crust of Crustacea, more preferably, 200–1200 mg; as one-day dose per 1 kg body weight of animal or human subject, administered or used as feed, veterinary pharmaceuticals, beverages, food, health food, and pharmaceuticals, or administered or used as ingredient thereof.

DETAILED DESCRIPTION OF THE PREFERRED EMBODIMENT

Peptides to be used for the present invention are derived from swine plasma by methods well known in the art. For example, add two-times the amount of deionized water to swine plasma powder, and adjust pH by 1N HCl to pH 2.0; then, add 2% pepsin, and hydrolyze at 37° for 24 hours. After reaction, filter the hydrolyzed solution through ultrafiltration membrane, and transfer the filtrate into DOWEX 50W column (Dow Chemicals, Richmond, Va.), a column of strong acid positive ion exchange resin; wash the column with deionized water, and dissolve peptide from column with 2N $NH_4OH$. Remove ammonia by vacuum concentration, and use the concentrate to repeat gel filtration column chromatography; the peptide is obtained by freeze-drying the peptide fraction from repeated filtration. Albumin can be obtained by the following method. That is, by centrifuging swine plasma, remove fibrinogen and globulin, and spray-drying the albumin fraction obtained from centrifuging.

In order to stimulate immune function and to prevent infectious disease and cancer, administration of peptide purified from swine plasma albumin at the daily dose at 1–300 mg, or more preferably, 5–100 mg, per 1 kg of animal or human body weight as feed, veterinary pharmaceuticals, beverages, food, health food, and pharmaceuticals, or administered or used as mixed ingredient of aforementioned is preferred. In the case of swine plasma albumin, it is preferable to similarly administer 30–1000 mg, or more preferably, 70–500 mg, per 1 kg of animal or human body weight, as the daily dose. In the case of swine plasma or swine plasma mixed with fine-powdered Crustacea or crust of Crustacea, it is preferable to similarly administer 100–3000 mg, more preferably, 200–1200 mg, per 1 kg body weight of animal or human body weight, as daily dose.

The subject Crustacea for the administration in the present invention include all Crustacea and include but are not limited to kuruma prawn, fleshy prawn, black tiger, and blue crab; the subject Pisces, includes all Pisces but is not limited to red sea bream, yellowtail, blow fish, flounder, eel, and rainbow trout; the subject animal includes all mammals and Aves but is not limited to swine, cattle, horse, sheep, chicken, dog, and cat; and humans including from infant to elderly. And infection means infections caused by all virus, Mycoplasma, rickettsia, bacteria, fungi, and parasite, that include but not limited to acute viremia of kuruma prawn group (White Spot syndrome), iridovirus infection of Pisces, tuberculoid and streptococcus infection of yellowtail, vibrionic disease, atrophic rhinitis and pleuropneumonia of swine, infectious bronchitis and $E.\ coli$ infection of fowl, feline leukemia, VRE infection, enterohemorrhagic $E.\ coli$ infection, tuberculosis, influenza of humans. Moreover, tumor means all types of polyps and all benign and malignant tumors such as lung cancer, breast cancer, pharyngeal cancer, liver cancer, pancreatic cancer, uterine cancer, and colon cancer.

The following examples are offered to illustrate but not limit the invention. Thus, they are presented with the understanding that various formulation modifications as well as reactor modifications may be made and still be within the spirit of the invention.

EXAMPLE 1

Stimulating Action on Immune Function (Phagocytotic Index of Corpuscle) of Crustacea—Appropriate Dose Determination Test Test Procedure To each of 19 groups, 15 Kuruma prawn, of average weight 20 g, are assigned, and as invention group, Group 1–6 were administered swine plasma-derived peptide (PE, hereafter), Group 7–12, swine plasma albumin (AL, hereafter), and Group 13–18, swine plasma (PL, hereafter), in dose indicated in Table 1, for period of 7 days, administered as a mixed ingredient in feed. For Group 19, as control group, animals were fed the feed without any of above substance mixed as ingredient. At the start of administration (0 day), 3 days and 7 days from the start, draw blood from antrum of prawn's chest using syringe containing K-199 medium with L-cysteine as anticoagulant, and obtained corpuscles from blood by centrifuging. For 1 ml of suspension, mix $5 \times 10^7$ pieces of latex beads (1.97 m diameter) to $5 \times 10^6$ cells of corpuscles; after allowing to react in 25 for 30 minutes, fixed them by glutaraldehyde, washed, and air dried. After air drying, stain by Giemsa staining, and fixed on a slide glass using Eukitt® (O. Kindler, Germany). Prepare 5 sample slides for each prawn; observe 200 corpuscles randomly selected by using fluorescent microscope, count the number of latex beads phagocytosed, and calculated phagocytotic index by the equation below.

Phagocytotic Index: (number of corpuscle phagocytosed latex beads/numbers of corpuscle observed)×(number of beads phagocytosed by corpuscle/numbers of corpuscle observed)×100

TABLE 1

Test Group and Applied Dose of Each Substance in Example 1

| Test Group | Substance Type | Applied Dose mg/kg(Body Weight) |
|---|---|---|
| Group 1 | PE (Swine plasma-derived peptide) | 0.5 |
| Group 2 | PE (Swine plasma-derived peptide) | 1.0 |
| Group 3 | PE (Swine plasma-derived peptide) | 5.0 |
| Group 4 | PE (Swine plasma-derived peptide) | 100 |
| Group 5 | PE (Swine plasma-derived peptide) | 300 |
| Group 6 | PE (Swine plasma-derived peptide) | 400 |
| Group 7 | AL (Swine plasma albumin) | 20 |
| Group 8 | AL (Swine plasma albumin) | 30 |
| Group 9 | AL (Swine plasma albumin) | 70 |
| Group 10 | AL (Swine plasma albumin) | 500 |
| Group 11 | AL (Swine plasma albumin) | 1000 |
| Group 12 | AL (Swine plasma albumin) | 2000 |
| Group 13 | PL (Swine plasma) | 50 |
| Group 14 | PL (Swine plasma) | 100 |
| Group 15 | PL (Swine plasma) | 200 |
| Group 16 | PL (Swine plasma) | 1200 |
| Group 17 | PL (Swine plasma) | 3000 |
| Group 18 | PL (Swine plasma) | 4000 |
| Group 19 | Control | 0 |

Test Results:

Phagocytotic index of kuruma prawns in groups administered the present invention and control group is shown in Table 2. Phagocytotic index of prawns administered each substance were increased after 3 days from the start of administration, and especially the activities were markedly high in 5 and 100 mg of PE, 70 and 500 mg of AL, and 200 and 1200 mg of PL, which differences to control group were statistically significant ($P<0.05$). After 7 days from the start of administration, phagocytotic index of the above dose groups of PE, AL, and PL further increased; while, the value of control group was 16.7±7.41, 5 mg Group was 67.5±10.34 and 100 mg Group was 85.1±12.15 for PE., 70 mg Group was 72.4±10.52 and 500 mg Group was 91.3±13.24 for AL, and 200 mg Group was 57.7±9.66 and 1200 mg Group was 64.6±10.32 for PL; and statistically significant difference was observed between these groups to control group ($P<0.01$). Also, the activities at 1 and 300 mg Group of PE, 30 and 1000 Group of AL, and 100 and 3000 Group of PL were relatively high, and statistically significant difference was observed between these groups to control group ($P<0.05$). From these results, we clarified that by administrations of swine plasma-derived peptide, plasma albumin, or plasma to Crustacea stimulate immune functions such as phagocytotic action of corpuscle; however, it was shown that there are upper and lower limit in the dose that is effective for stimulation. That is, it was clarified that the appropriate doses to stimulate immune function are 1–300 mg/kg (body weight) for PE, 300–1000 mg/kg (body weight) for AL, and 100–3000 mg/kg (body weight) for PL; the optimum doses are 5–100 mg for PE, 70–500 mg for AL, and 200–1200 mg for PL.

TABLE 2

Phagocytotic Index of Kuruma Prawn Corpuscle in Invention and Control Groups

| Test Group | Phagocytotic Index of Corpuscle | | |
|---|---|---|---|
| | Start of administration (0 day) | 3 days from the start | 7 days from the start |
| Group 1 PE 0.5 mg | 14.2 ± 4.09 | 16.3 ± 5.84 | 17.0 ± 8.44 |
| Group 2 PE 1.0 mg | 15.0 ± 4.65 | 23.4 ± 5.32 | 33.4 ± 7.27 *1 |
| Group 3 PE 5.0 mg | 12.8 ± 3.56 | 28.7 ± 6.10 *1 | 67.5 ± 10.34 *2 |
| Group 4 PE 100 mg | 13.4 ± 5.11 | 37.5 ± 8.02 *1 | 85.1 ± 12.15 *2 |
| Group 5 PE 300 mg | 16.1 ± 7.02 | 22.9 ± 5.72 | 36.2 ± 6.68 *1 |
| Group 6 PE 400 mg | 15.7 ± 6.32 | 15.7 ± 4.66 | 18.7 ± 7.04 |
| Group 7 AL 20 mg | 15.4 ± 5.95 | 17.4 ± 5.83 | 17.8 ± 6.52 |
| Group 8 AL 30 mg | 14.8 ± 6.06 | 24.6 ± 7.16 | 37.4 ± 9.21 *1 |
| Group 9 AL 70 mg | 15.2 ± 6.27 | 30.4 ± 6.72 *1 | 72.4 ± 10.52 *2 |
| Group 10 AL 500 mg | 13.8 ± 4.83 | 35.7 ± 7.45 *1 | 91.3 ± 13.24 *2 |
| Group 11 AL 1000 mg | 15.4 ± 7.14 | 26.1 ± 9.22 | 41.2 ± 9.75 *1 |
| Group 12 AL 2000 mg | 16.2 ± 5.86 | 14.6 ± 4.53 | 18.5 ± 6.26 |
| Group 13 PL 50 mg | 14.7 ± 4.99 | 15.7 ± 6.18 | 16.7 ± 5.47 |
| Group 14 PL 100 mg | 13.8 ± 7.32 | 22.9 ± 7.36 | 34.6 ± 7.83 *1 |
| Group 15 PL 200 mg | 15.4 ± 5.67 | 28.5 ± 5.26 *1 | 57.7 ± 9.66 *2 |
| Group 16 PL 1200 mg | 14.7 ± 4.82 | 29.8 ± 5.34 *1 | 64.6 ± 10.32 *2 |
| Group 17 PL 3000 mg | 13.6 ± 6.25 | 21.3 ± 6.85 | 31.9 ± 6.23 *1 |
| Group 18 PL 4000 mg | 15.2 ± 5.81 | 16.4 ± 7.25 | 17.2 ± 5.47 |
| Group 19 Control | 16.3 ± 6.33 | 15.3 ± 5.67 | 16.7 ± 7.41 |

*1 Significant difference from Control Group (P < 0.05).
*2 Significant difference from Control Group (P < 0.01).

EXAMPLE 2

Effect on Immune Function (Phenol Oxidase Activity) of Crustacean

Test Procedure:

To each of 13 groups, 15 Kuruma prawn, of average weight 18 g, are assigned, and as invention group, Group 1–4 were administered PE, Group 5–8, AL, Group 9–12, PL, also, swine globulin to Group 13, and bovine globulin to Group 14 for period of 7 days, administered as a mixed ingredient in feed. For Group 15, as control group, animals were fed the feed without any of above substance mixed as ingredient. At the start of administration (0 day), 3 days and 7 days from the start draw blood from antrum of prawn's chest, using syringe containing KHE medium with EDTA as anticoagulant, centrifuged and corpuscles were obtained. Suspend these corpuscles in Ca—Mg HEPES medium to be $1\times10^6$ cells, perform hemolysis by freezing and destroy by sonication, filter the supernatant from centrifuging, using membrane filter. Mix 900 l of this filtrate and 100 l of L-DOPA solution as substrate, and let it react in 60 for 60 minutes; using spectrophotometer, determine the absorption at 490 nm, as phenol oxidase (PO) activity.

TABLE 3

Test Group and Applied Dose of Each Substance in Example 2

| Test Group | Substance Type | Applied Dose mg/kg (Body Weight) |
|---|---|---|
| Group 1 | PE | 0.5 |
| Group 2 | PE | 20 |
| Group 3 | PE | 50 |
| Group 4 | PE | 400 |
| Group 5 | AL | 20 |
| Group 6 | AL | 150 |
| Group 7 | AL | 400 |
| Group 8 | AL | 2000 |
| Group 9 | PL | 50 |
| Group 10 | PL | 400 |
| Group 11 | PL | 1000 |
| Group 12 | PL | 4000 |
| Group 13 | SG (Swine globulin) | 400 |
| Group 14 | BG (Bovine globulin) | 400 |
| Group 15 | Control | 0 |

Immune function of Crustacea is composed of cellular and humoral factors; since phagocytotic ability (or index) to foreign matter (pathogen) as described in Embodiment 1 relates to the former, and PO activity of corpuscle relates to the latter, it has been commonly known that activation of Crustacean immune function is determined by testing for phagocytotic index of Embodiment 1 or PO activity of Embodiment 2 [Takahashi Y et al. Gyobyoukennkyuu, (Ichthyic Disease Research, in Japanese). 1995;30:141–150]. Therefore, in order to determine whether the immune function of prawn that was administered the said substance of present invention, we investigated phagocytotic index and PO activity.

Test Results:

PO activity of kuruma prawns in groups administered the present invention and the control group is shown in Table 4. PO activity of prawns administered each substance were increased after 3 days from the start of administration, and especially the activities were markedly high in 20 mg of PE, 150 mg of AL, and 400 mg of PL, which differences to control group were statistically significant (P<0.01). After 7 days from the start of administration, PO activity of the above dose groups further increased; while, the value of control group was 0.27±0.063, 20 mg PE Group was 1.25±0.106, 150 mg AL Group was 1.14±0.083, and 400 mg PL Group was 1.03±0.083. Also, the activities of 50 mg PE Group, 400 mg AL Group, and 1000 mg PL Group were high, and statistically significant difference was observed between these groups to control group (P<0.01). However, groups as 0.5 and 400 mg PE, 20 and 2000 mg AL, and 50 and 4000 mg PL had low activities; therefore, as clarified in Embodiment 1, it was suggested that said substance of present invention do not stimulate immune function unless administered in appropriate dose. Moreover, 400 mg SG Group and 400 mg BG Group had not shown any change; therefore, we consider that globulin do not contain substance that stimulate immune function of prawn.

TABLE 4

Phenol Oxidase Activity of Kuruma Prawn Corpuscle in Example 2

| Test Group | P. O. Activity (Absorption at 490 nm) | | |
|---|---|---|---|
| | Start of administration (0 day) | 3 days from the start | 7 days from the start |
| Group 1 PE 0.5 mg | 0.21 ± 0.042 | 0.28 ± 0.046 | 0.23 ± 0.051 |
| Group 2 PE 20 mg | 0.19 ± 0.051 | 0.71 ± 0.083 *2 | 1.25 ± 0.106 *2 |
| Group 3 PE 50 mg | 0.26 ± 0.033 | 0.45 ± 0.062 *1 | 0.86 ± 0.073 *2 |
| Group 4 PE 400 mg | 0.20 ± 0.057 | 0.30 ± 0.075 | 0.25 ± 0.046 |
| Group 5 AL 20 mg | 0.29 ± 0.072 | 0.22 ± 0.048 | 0.27 ± 0.037 |
| Group 6 AL 150 mg | 0.18 ± 0.042 | 0.68 ± 0.070 *2 | 1.14 ± 0.083 *2 |
| Group 7 AL 400 mg | 0.22 ± 0.063 | 0.44 ± 0.067 *1 | 0.79 ± 0.096 *2 |
| Group 8 PL 50 mg | 0.25 ± 0.048 | 0.27 ± 0.049 | 0.28 ± 0.072 |
| Group 9 PL 50 mg | 0.23 ± 0.062 | 0.21 ± 0.044 | 0.20 ± 0.037 |
| Group 10 PL 400 mg | 0.27 ± 0.051 | 0.82 ± 0.103 *2 | 1.03 ± 0.085 *2 |
| Group 11 PL 1000 mg | 0.22 ± 0.038 | 0.46 ± 0.056 *1 | 0.92 ± 0.115 *2 |
| Group 12 PL 4000 mg | 0.24 ± 0.072 | 0.21 ± 0.063 | 0.29 ± 0.064 |
| Group 13 SG 400 mg | 0.22 ± 0.051 | 0.20 ± 0.063 | 0.24 ± 0.054 |
| Group 14 BG 400 mg | 0.24 ± 0.038 | 0.23 ± 0.046 | 0.26 ± 0.072 |
| Group 15 Control | 0.25 ± 0.066 | 0.23 ± 0.057 | 0.27 ± 0.063 |

*1 Significant difference from Control Group ($P < 0.05$).
*2 Significant difference from Control Group ($P < 0.01$).

EXAMPLE 3

Preventative Effect on White Spot Syndrome of Kuruma Prawn

Test Procedure:

To each of 13 groups, 20 Kuruma prawn, of average weight 9 g, are assigned, and as invention groups, Group 1–12 were administered of the said substances as the daily dose per 1 kilogram of yellowtail's body weight shown in Table 3, for period of 18 days, administered as a mixed ingredient in feed. For Group 13, as control group, animals were fed the feed without any of the above substance mixed as ingredient. Eight days after the start of administering each substance, prawns from each group were infected with WSSV (white spot syndrome virus), the causative virus of white spot syndrome, by submerged in virus suspended seawater for 2 hours. After 10 days from infecting, the number of dead shrimps were counted, and for those dead shrimps, pathological examination and detection of viral DNA, using PCR (polymerase chain reaction) method, to confirm whether the death was caused by this disease.

Test Results:

Numbers of dead shrimps and mortality rates of invention and control groups 10 days after viral infection are shown in Table 5. Mortality rate after viral challenge was 95% in Control Group; however, in 20 and 50 mg PE, 150 and 400 mg AL, and 400 and 1000 mg PL groups were as extremely low as 10–25%, and statistically significant differences between these groups and Control Group were observed ($P<0.01$). Thus, we have confirmed from results of Embodiment 1 and 2, and of this test, the substance of present invention shows excellent preventive effect of white spot syndrome by enhancing immune function of Crustacea.

TABLE 5

Numbers of Dead Shrimps and Mortality Rates After Viral Infection

| Test Group | Number of Dead Shrimps/Number of Subject Shrimps | Mortality Rate (%) |
|---|---|---|
| Group 1 PE 0.5 mg | 18/20 | 90 |
| Group 2 PE 20 mg | 2/20 | 10* |
| Group 3 PE 50 mg | 4/20 | 20* |
| Group 4 PE 400 mg | 17/20 | 85 |
| Group 5 AL 20 mg | 19/20 | 95 |
| Group 6 AL 150 mg | 3/20 | 15* |
| Group 7 AL 400 mg | 5/20 | 25* |
| Group 8 PL 2000 mg | 18/20 | 90 |
| Group 9 PL 50 mg | 20/20 | 100 |
| Group 10 PL 400 mg | 2/20 | 10* |
| Group 11 PL 1000 mg | 4/20 | 20* |
| Group 12 PL 4000 mg | 20/20 | 100 |
| Group 13 Control | 19/20 | 95 |

*Significant difference from Control Group ($P < 0.01$).

EXAMPLE 4

Preventative Effect on Streptococcus Infection of Yellowtail

Test Procedure:

To each of 9 groups, 20 yellowtails, of average weight 175 g, were assigned, and as invention groups, Group 1–8 were administered of the said substances of present invention as the daily dose per 1 kilogram of yellowtail's body weight an in Table 6, for period of 30 days, as a mixed ingredient in feed as to achieve the dose levels shown in Table 6. For Group 9, as control group, animals were fed the feed without any of the above substances mixed as ingredient. Eight days after the start of administering each substance, we inoculated intraperitoneally to each individual yellowtail, $3.0 \times 10^6$ cells of *Lactococcus garvieae*, the causative bacteria of streptococcus infection, to each individual yellowtail, and mortality rates were determined for 22 days after inoculation.

TABLE 6

Test Group and Applied Dose of Each Substance in Example 4

| Test Group | Substance Type | Applied Dose mg/kg(Body Weight) |
|---|---|---|
| Group 1 | PE | 20 |
| Group 2 | PE | 50 |
| Group 3 | AL | 150 |
| Group 4 | AL | 400 |
| Group 5 | PL | 100 |
| Group 6 | PL + euphausiid powder | 90 + 10 |
| Group 7 | PL | 400 |
| Group 8 | PL | 1000 |
| Group 9 | Control | 0 |

Test Results:

The numbers of dead yellowtails (Dead Fish) and mortality rates of present invention groups and control group after inoculation of pathogenic bacteria are shown in Table 7. Mortality rate for period of 22 days after inoculation of pathogenic bacteria was 85% for control group; however, those rates in invention groups were as low as 5–45%, and statistically significant differences were observed between invention groups and control group (P<0.05 or 0.01). Especially, the mortality rates in 20 mg PE, 150 mg AL, and 400 mg PL groups were markedly low (P<0.01). From above results, swine plasma and swine plasma-derived albumin and peptide have shown preventive effect on infectious disease of Pisces, in addition to that of Crustacea. Moreover, we have discovered that the concomitant use of powdered Crustacea (euphausiid) further enhances the effect. As the cause of this effect, we consider that the synergistic effect of peptide in swine plasma and astaxanthin or chitin in euphausiid activate the immune function of yellowtail even more.

TABLE 7

Numbers of Dead Fish and Mortality Rates After Pathogenic Bacteria Inoculation in Example 4

| Test Group | Number of Dead Fish/Number of Subject Fish | Mortality Rate (%) |
| --- | --- | --- |
| Group 1 PE 20 mg | 1/20 | 5 *2 |
| Group 2 PE 50 mg | 3/20 | 15 *2 |
| Group 3 AL 150 mg | 2/20 | 10 *2 |
| Group 4 AL 400 mg | 4/20 | 20 *2 |
| Group 5 PL 100 mg | 9/20 | 45 *1 |
| Group 6 PL 90 mg + euphausiid powder 10 mg | 4/20 | 20 *2 |
| Group 7 PL 400 mg | 1/20 | 5 *2 |
| Group 8 PL 1000 mg | 5/20 | 25 *2 |
| Group 9 Control | 17/20 | 85 *2 |

*1 Significant difference from Control Group (P < 0.05).
*2 Significant difference from Control Group (P < 0.01).

EXAMPLE 5

Activating Effect Toward Immune Function (Phagocytotic Activity of Mouse Neutrophil) of Mammals Including Humans Test Procedure:

To each of 15 groups, 12 ICR mouse of SPF (7-week old), were assigned, and as present invention groups, Group 1–14 were administered of the said substances as the daily dose per 1 kilogram of mouse's body weight as in Table 8, for period of 7 days, as a mixed ingredient in feed as to achieve the dose levels shown in Table 8. For Group 15, as control group, animals were fed the feed without any of the above substances mixed as ingredient. At the start of administration (0 day), 3 days and 7 days from the start, blood samples were drawn from 4 mouse in each group, collected neutrophils by percoll discontinuous density gradient method; then, determined the number of phagocytosed yeast cells by mouse neutrophils, and phagocytotic index was determined by using the same equation.

TABLE 8

Test Group and Applied Dose of Each Substance in Example 5

| Test Group | Substance Type | Applied Dose mg/kg(Body Weight) |
| --- | --- | --- |
| Group 1 | PE | 0.5 |
| Group 2 | PE | 20 |
| Group 3 | PE | 50 |
| Group 4 | PE | 400 |
| Group 5 | AL | 20 |
| Group 6 | AL | 150 |
| Group 7 | AL | 400 |
| Group 8 | AL | 2000 |
| Group 9 | PL | 50 |
| Group 10 | PL | 100 |
| Group 11 | PL + euphausiid powder | 90 + 10 |
| Group 12 | PL | 400 |
| Group 13 | PL | 1000 |
| Group 14 | PL | 4000 |
| Group 15 | Control | 0 |

Test Results:

The numbers of phagocytotic index in invention groups and control group are shown in Table 9. Phagocytotic index of mouse neutrophils in invention groups began to increase from 3 days from the start of administration, and activation of 20 mg PE, 150 mg and 400 mg AL, and 400 mg PL were especially high, showing statistically significant differences between these groups and control group (P<0.01). After 7 days from the start of administration, these groups were observed with even higher activation, and additionally, the activation at 50 mg PE, 90 mg PL+10 mg euphausiid powder, and 1000 mg PL groups were markedly high (P<0.01). From above results, it was clarified that the said substances of present invention have activating effect on immune functions of Mammals, in addition to that of Crustacea. Moreover, we have discovered that the mixed use of powdered Crustacea (euphausiid) markedly enhances the immune function, compared to single use of swine plasma. As the cause of this effect, as we already described in Embodiment 4, we consider that the phenomenon owes to the synergistic effect of peptide in swine plasma and astaxanthin or chitin in euphausiid. For experimental data, only that of swine plasma and powdered Crustacea (euphausiid) mixture are shown; however, cases using the mixture of swine plasma albumin and powdered Crustacea, and the mixture of peptides purified from swine plasma or swine plasma albumin and powdered Crustacea similarly enhance immune function. Preferred ratio of mixings are approximately 95%:5% to 80%:20%, in case of mixing swine plasma and powdered Crustacea (euphausiid). Furthermore, in cases of using astaxanthin or chitin purified from Crustacea or crust of Crustacea, small amounts are required to be effective. On the other hand, the activities of 0.5 mg and 400 mg PE, 20 mg and 2000 mg AL, and 50 mg and 4000 mg PE group did not increase; therefore, there are upper limit and lower limit in the dose, in order for the said substances of present invention to show the effect.

TABLE 9

Phagocytotic Index of Mouse Neutrophil in Example 5

| Test Group | Start of Administration (0 day) | 3 Days from the Start | 7 Days from the Start |
| --- | --- | --- | --- |
| Group 1 PE 0.5 mg | 22.4 ± 3.52 | 23.7 ± 4.26 | 24.3 ± 4.51 |
| Group 2 PE 20 mg | 20.1 ± 2.07 | 46.3 ± 7.34 *2 | 106.2 ± 11.05 *2 |

TABLE 9-continued

Phagocytotic Index of Mouse Neutrophil in Example 5

| Test Group | Start of Administration (0 day) | 3 Days from the Start | 7 Days from the Start |
|---|---|---|---|
| Group 3 PE 50 mg | 24.2 ± 4.13 | 33.6 ± 4.19 *1 | 78.8 ± 6.14 *2 |
| Group 4 PE400 mg | 19.2 ± 2.97 | 24.2 ± 5.20 | 25.0 ± 4.76 |
| Group 5 AL 20 mg | 18.7 ± 2.05 | 22.5 ± 3.81 | 24.6 ± 3.81 |
| Group 6 AL 150 mg | 25.3 ± 3.82 | 52.1 ± 9.52 *2 | 92.4 ± 8.66 *2 |
| Group 7 AL 400 mg | 19.4 ± 2.72 | 44.8 ± 5.73 *2 | 78.5 ± 6.81 *2 |
| Group 8 AL 2000 mg | 22.5 ± 3.22 | 23.4 ± 3.63 | 25.3 ± 5.11 |
| Group 9 PL 50 mg | 20.7 ± 2.76 | 25.1 ± 5.72 | 23.8 ± 4.07 |
| Group 10 PL 100 mg | 21.3 ± 2.52 | 26.2 ± 3.45 | 39.4 ± 5.32 *1 |
| Group 11 PL 90 mg + euphausiid powder 10 mg | 23.4 ± 3.02 | 30.7 ± 3.18 *1 | 77.6 ± 7.19 *2 |
| Group 12 PL 400 mg | 20.7 ± 2.71 | 50.6 ± 8.73 *2 | 97.4 ± 11.62 *2 |
| Group 13 PL 1000 mg | 24.0 ± 5.02 | 35.2 ± 6.64 *1 | 86.2 ± 7.35 *2 |
| Group 14 PL 4000 mg | 21.7 v 3.27 | 25.7 ± 4.16 | 27.4 ± 6.51 |
| Group 15 Control | 23.4 ± 2.73 | 21.7 ± 3.06 | 24.2 ± 5.08 |

*1 Significant difference from Control Group (P < 0.05).
*2 Significant difference from Control Group (P < 0.01).

EXAMPLE 6

Preventive Effect on Infection of Mammals Including Human—Effective Dose Determination Test by *E. coli* Infection of Mouse as Experimental Model—

Test Procedure:

To each of 19 groups, 15 ICR mouse of SPF (7-week old), were assigned, and as invention group, Group 1–18 were administered of the said substances as the daily dose per 1 kilogram of mouse's body weight as in Table 1 of Embodiment 1, for period of 15 days, as a mixed ingredient in feed as to achieve the dose levels shown in Table 1. On 8 days after the start of administration, $7.0 \times 10^7$ cells of *E. coli* were inoculated intraperitoneally to each individual mouse, and the effective doses of said substances of present invention were determined by mortality rates for up to 7 days from inoculation.

Test Results:

The numbers of dead mouse and mortality rates of invention groups and control group after inoculation of *E. coli* are shown in Table 10. Mortality rate was 93.3% for control group; however, those rates in most invention groups were tend to be low, and especially, the mortality rates in 5 mg and 100 mg PE, 70 mg and 500 mg AL, and 200 mg and 1200 mg PL groups were markedly low as 20.0–33.3%, with statistically significant differences between these invention groups and control group (P<0.01). Also, relatively low mortality rates were observed in 1 mg and 300 mg PE, 30 mg and 1000 mg AL, and 100 mg and 3000 mg PL, and statistically significant difference were observed (P<0.01); however, no preventive effect was identified in 0.5 mg and 400 mg PE, 20 mg and 2000 mg AL, and 50 mg and 4000 mg PL groups. From above results, appropriate dose of the said substances of present invention are presumed to be 1–300 mg/kg (body weight)/day for PE, 30–1000 mg/kg (body weight)/day for AL, and 200–1200 mg/kg (body weight)/day for PL; and optimum doses are presumed to be 5–100 mg for PE, 70–500 mg for AL, and 200–1200 mg for PL.

TABLE 10

Numbers of Dead Mouse and Mortality Rates 7 Days After *E. coli* Inoculation in Example 6

| Test Group | Number of Dead Mouse/ Number of Subject Mouse | Mortality Rate (%) |
|---|---|---|
| Group 1 PE 0.5 mg | 15/15 | 100.0 |
| Group 2 PE 1.0 mg | 8/15 | 53.3 *1 |
| Group 3 PE 5.0 mg | 5/15 | 33.3 *2 |
| Group 4 PE 100 mg | 4/15 | 26.7 *2 |
| Group 5 PE 300 mg | 7/15 | 46.7 *1 |
| Group 6 PE 400 mg | 13/15 | 86.7 |
| Group 7 AL 20 mg | 13/15 | 86.7 |
| Group 8 AL 20 mg | 7/15 | 46.7 *1 |
| Group 9 AL 70 mg | 4/15 | 26.7 *2 |
| Group 10 AL 500 mg | 3/15 | 20.0 *2 |
| Group 11 AL 1000 mg | 8/15 | 53.3 *1 |
| Group 12 AL 2000 mg | 12/15 | 80.0 |
| Group 13 PL 50 mg | 15/15 | 100.0 |
| Group 14 PL 100 mg | 9/15 | 60.0 *1 |
| Group 15 PL 200 mg | 5/15 | 33.3 *2 |
| Group 16 PL 1200 mg | 4/15 | 26.7 *2 |
| Group 17 PL 3000 mg | 7/15 | 46.7 *1 |
| Group 18 PL 4000 mg | 14/15 | 93.3 |
| Group 19 Control | 14/15 | 93.3 |

*1 Significant difference from Control Group (P < 0.05).
*2 Significant difference from Control Group (P < 0.01).

EXAMPLE 7

Preventive Effect on Diarrhea (*E. coli* Infection) of Piglets

Test Procedure:

Total of 48 piglets, which were farrowed from 5 sows produced within the similar time period at open-air swinery, were separated in two groups of 24 piglets each, after feeding on colostrum, in the allocation manner that there should be no difference in sex and body weight between two groups, and each farrow distributed equally; then, the Group 1 of invention groups was administered of albumin (AL) isolated from swine plasma at daily dose of 200 mg per 1 kg body weight of piglet, for 35 days mixed into milk replacer. The Group 2 of control group was fed the milk replacer without the said substance. Also, for the albumin group of present invention groups, the albumin was used after confirming that antibody (immunoglobulin) against *E. coli* or any substance with antibacterial activities was not included. The incidence rates of diarrhea caused by *E. coli* was determined for 35 days after the start of administration.

Test Results:

The incidence rates of *E. coli* infection in invention groups and control group for 35 days are shown in Table 11. In control group, the incidence rate was 37.5%; however, in the present invention group, it was as low as 8.3%, and statistically significant difference was observed between the invention and control group (P<0.05). Since no substance such as antibody against *E. coli* or any substance with antibacterial activities is included in milk replacer fed to the present invention group, the said substance of present invention is considered to prevent *E. coli* infection by activating immune function of piglets.

TABLE 11

Incidence Rate of Diarrhea (E. coli Infection) Among Piglets in Example 7

| Test Group | Number of Piglet Developed the Infection/ Number of Subject Piglet | Incidence Rate (%) |
| --- | --- | --- |
| Group 1 AL 200 mg | 2/24 | 8.3* |
| Group 2 Control | 9/24 | 37.5* |

*Significant difference from Control Group (P < 0.05).

EXAMPLE 8

Expression of Antitumor Activity

Test Procedure:

To each 4 group, 15 (6-week old) BALB/C mouse were assigned, and 25 mg of PE was administered to Group 1 of invention groups, 150 mg AL to Group 2, and 400 mg PL to Group 3, as daily dose per 1 kg of mouse body weight, for 28 days as mixed ingredient in feed. Group 4 of control group was fed the feeds without any of the above substances included. On $7^{th}$ day from the start of administrating those feed, Meth-A tumor cells at the amount of $1 \times 10^6$ cells/mouse were inoculated intraperitoneally; then, 21 days after inoculation, presence or absence of tumor cell proliferation was observed, and expression effect of antitumor activity was evaluated.

Test Result:

Presence or absence of tumor was observed in present invention groups or control group mouse and the results as suppression rate of tumor proliferation are shown in Table 12. The number of mouse identified with tumor due to its proliferation, on 21 days after inoculation of Meth-A tumor cells, was 12 in control group; however, 3 in 25 mg PE group, 1 in 150 mg AL group, and 4 in 400 mg PL group. Suppression rate of tumor proliferation was 20% in control group; however, the rates in invention groups were markedly high as 80.0% in 25 mg PE, 93.3% in 150 mg AL, and 73.3% in 400 mg PL group, and all groups had statistically significant differences between control groups (P<0.01). Thus, we clarified that the said substances of present invention show suppression effect of tumor proliferation, in addition to preventing infection, by activating immune function of animal.

TABLE 12

Suppression Rate of Tumor Proliferation After Tumor Cell Inoculation in Example 8

| Test Group | Number of Mouse with Identified Tumor/ Number of Subject Mouse | Suppression Rate of Tumor Proliferation (%) |
| --- | --- | --- |
| Group 1 PE 25 mg | 3/15 | 80.0* |
| Group 2 AL 150 mg | 1/15 | 93.3* |
| Group 3 PL 400 mg | 4/15 | 73.3* |
| Group 4 Control | 12/15 | 20.0* |

*Significant difference from Control Group (P < 0.01).

EXAMPLE 9

Preventative Effect on Common Cold and Influenza

Test Procedures:

From December 15 to March 15, during the 3-month period when common cold and influenza epidemic are prevalent, out of 126 elementary school children (62 boys and 64 girls; average weight 28.1 kg), 63 (31 boys and 32 girls) were administered of 0.7 g peptide purified from swine albumin as daily dose per child (approximately 25 mg/kg body weight), for 3 months. Other 63 were administered of 0.7 mg lactose as daily dose per one child, for 3 months. During the 3-month period, those experienced symptoms such as chill, nasal discharge, cough, headache, fever, and diarrhea were examined by medical doctor without exception, and the number of children identified with common cold or influenza were recorded to obtain the incidence rates of both diseases.

Test Results:

Incidence rates of common cold or influenza in present invention groups and control group during 3 months are shown in Table 13. An incidence rate of common cold or influenza was 34.9% in control group; however, the incidence rate of children in PE administered group was as low as 11.1%, and statistically significant difference was observed (P<0.05). From above results, it was clarified that the said substances of present invention have preventive effect on infectious disease in humans, in addition to that on fishes and shellfishes and other animals.

TABLE 13

Incidence Rate of Common cold or Influenza in Example 9

| Test Group | Number of Diagnosed Patients/Number of Subjects | Incidence Rate (%) |
| --- | --- | --- |
| Group 1 PE 0.79 g Administered | 7/63 | 11.1* |
| Group 2 Control, Lactose Administered | 22/63 | 34.9 |

*Significant difference from Control Group (P < 0.05).

As described above, immunostimulator for animals and humans of present invention, includes swine plasma or peptides present in swine plasma albumin as active ingredients. The invented substances also include the mixture swine plasma powder, albumin or peptides and fine powder of Crustacea (or crust of Crustacea) or the purified materials of Crustacea or crust of Crustacea as active ingredients. The methods of preventing infection and cancer of animal and humans, in present invention, are to administer at least one but not limited to one from swine plasma, swine plasma albumin, peptides isolated or purified swine plasma or swine plasma albumin, and swine plasma including fine powder of Crustacea (including crust of Crustacea) in the rate of 10%; and to use by administrating in the designated daily dose per 1 kg body weight of animal or humans as the form or mixed content in feed, veterinary pharmaceuticals, beverages, food, health food, and pharmaceuticals.

At the same time, present invention shows marked effect in preventing infection and cancer in Crustacea, Pisces, Aves, Mammals, and humans, by the use or administration in appropriate dose, of swine plasma, peptides included in swine plasma albumin, swine plasma, albumin, and peptides mixture including fine powder of Crustacea (including crust of Crustacea) or purified materials from Crustacea or crust of Crustacea, bringing the action of granulocyte of Crustacea, leukocyte of Pisces, and macrophage, neutrophil, natural killer cell, T lymphocyte, and B lymphocyte of Mammals and humans, consequently fortifying non-specific and specific bio-defense mechanisms such as phagocytotic activity, complement activity, lysozyme activity, phenol oxidase activity, cytokine production ability, and antibody production ability.

Therefore, the present invention reliably prevents diseases of cultured fishes and shellfishes and livestock, and contributes greatly to aquaculture industry and livestock industry. Also, for humans, present invention activates immune functions, and increases the disease resisting power.

Moreover, immunostimulators of present invention show superior effect in immunostimulation, prevention of infection, and cancer prevention by very small amount, therefore economical; there is an advantage that needs to use pricey conventional antibiotics are almost none. Furthermore, said immunostimulators have various outstanding effect such as it can be used flexibly as additives in feed, veterinary pharmaceuticals, beverages, food, health food, and pharmaceuticals, and efficiently administered and used.

We claim:

1. A method of activating non-specific immune functions or fortifying non-specific biodefense mechanisms in a human, or an animal selected from the group consisting of Crustaceae, Pisces, Aves, swine, horse, dog, and cat, comprising administering to the animal or the human an immunostimulating effective daily dose of between 100 to 3000 mg of isolated swine plasma per kg body weight of the human or the animal, wherein the non-specific biodefense mechanisms are selected from phagocytic activity, phenol oxidase activity, antitumor activity, complement activity, lysozyme activity, cytokine production ability, and antibody production ability.

2. The method according to claim 1, wherein the dose of swine plasma is between 200 to 1200 mg/kg body weight of the human or the animal.

3. The method of claim 1, wherein the swine plasma is mixed with fine-powdered Crustaceae or crust of Crustacea.

4. The method according to claim 1, wherein the swine plasma is administered through feed, veterinary pharmaceuticals, beverages, food, health food, or pharmaceuticals.

* * * * *